(12) United States Patent
Sakaki (10) Patent No.: US 10,517,977 B2
(45) Date of Patent: Dec. 31, 2019

(54) ULTRASONIC DECONTAMINATION DEVICE

(71) Applicant: NITTA CORPORATION, Osaka (JP)

(72) Inventor: Akio Sakaki, Aichi (JP)

(73) Assignee: NITTA CORPORATION, Osaka (JP)

( * ) Notice: Subject to any disclaimer, the term of this patent is extended or adjusted under 35 U.S.C. 154(b) by 2 days.

(21) Appl. No.: 14/796,433

(22) Filed: Jul. 10, 2015

(65) Prior Publication Data

US 2016/0022852 A1  Jan. 28, 2016

(30) Foreign Application Priority Data

Jul. 18, 2014 (JP) ................................ 2014-147883

(51) Int. Cl.
| A61L 2/22 | (2006.01) |
|---|---|
| A61L 2/20 | (2006.01) |
| A61L 9/12 | (2006.01) |
| A61L 9/14 | (2006.01) |
| A61L 2/24 | (2006.01) |

(52) U.S. Cl.
CPC .............. *A61L 2/22* (2013.01); *A61L 2/20* (2013.01); *A61L 2/24* (2013.01); *A61L 9/122* (2013.01); *A61L 9/14* (2013.01); *A61L 2/208* (2013.01); *A61L 2202/13* (2013.01); *A61L 2202/14* (2013.01); *A61L 2202/25* (2013.01); *A61L 2209/111* (2013.01); *A61L 2209/132* (2013.01); *A61L 2209/135* (2013.01); *A61L 2209/211* (2013.01)

(58) Field of Classification Search
CPC ....................................................... A61L 2/22
USPC ........................................................... 422/28
See application file for complete search history.

(56) References Cited

U.S. PATENT DOCUMENTS

| 8,382,008 B1 | 2/2013 | Ricciardi et al. | |
|---|---|---|---|
| 9,408,931 B1* | 8/2016 | Ricciardi | A61L 2/16 |
| 2004/0215046 A1* | 10/2004 | McVey | A61L 2/208 |
| | | | 423/582 |
| 2004/0256330 A1* | 12/2004 | Okazaki | A61L 2/16 |
| | | | 210/756 |

(Continued)

FOREIGN PATENT DOCUMENTS

| EP | 2759308 | 7/2014 |
|---|---|---|
| EP | 1 701 746 | 7/2015 |

(Continued)

OTHER PUBLICATIONS

Smilanick et al., Performance of fogged disinfectants to inactivate conidia of Penicillium digitatum within citrus degreening rooms, Dec. 2013, Postharvest Biology and Technology, 91, pp. 131-140.*

(Continued)

*Primary Examiner* — Kevin Joyner
*Assistant Examiner* — Holly M Mull
(74) *Attorney, Agent, or Firm* — Greenblum & Berstein, P.L.C.

(57) ABSTRACT

A device and method for decontaminating the interior of a biosafety cabinet using a drug considered to be safe for humans is provided. A device for decontaminating the interior of a biosafety cabinet includes an ultrasonic atomizer for atomizing a peracetic acid disinfectant using ultrasound and releasing droplets; a diffusion fan; a circulation fan; a temperature-humidity sensor; and a controller.

6 Claims, 3 Drawing Sheets

| | PREFERENCE |
|---|---|
| (a) | REFERENCE TEMPERATURE ($T_1$) AND REFERENCE HUMIDITY ($H_1$) SET, EFFECTIVE DECONTAMINATION TIME ($t_1$) AT SET DECONTAMINATION HUMIDITY (H) MEASURED MULTIPLE TIMES AND ESTABLISHED. |
| (b) | DRUG SPRAY AMOUNT FOUND FROM RATIO OF REFERENCE HUMIDITY ($H_1$) AND POSSIBLE HUMIDITY TO REFERENCE TEMPERATURE ($T_1$) AND SATURATED WATER VAPOR AMOUNT $a(T_1)$. |
| (c) | DRUG SPRAY AMOUNT FOUND FROM RATIO OF INITIAL HUMIDITY ($H_0$) AND POSSIBLE HUMIDITY TO INITIAL TEMPERATURE ($T_0$) AND SATURATED WATER VAPOR AMOUNT $a(T_0)$. |
| (d) | DRUG RATIO OF REFERENCE TEMPERATURE-HUMIDITY AND INITIAL TEMPERATURE-HUMIDITY FOUND FROM RATIOS OF (b) AND (c). |
| (e) | INITIAL TEMPERATURE-HUMIDITY AT (c) HUMIDIFIED WITH DRUG UP TO SET DECONTAMINATION HUMIDITY (H), EFFECTIVE DECONTAMINATION TIME MEASURED MULTIPLE TIMES AND ESTABLISHED. |
| (f) | RATIO OF DRUG IN (d) MULTIPLIED BY EFFECTIVE DECONTAMINATION TIME ($t_1$) IN (a). |
| (g) | WEIGHTING TEMPERATURE AND HUMIDITY, TEMPERATURE COEFFICIENT ($\alpha$) AND HUMIDITY COEFFICIENT ($\beta$) FOUND AND MULTIPLIED SO THAT (f) $\neq$ (e). |
| (h) | ADD TIME ($t_2$) FOR SUPPLEMENTATION EQUIVALENT TO ERROR OF HUMIDITY GAUGE SENSOR IN (g). |
| (i) | ANY DECONTAMINATION TIME ($t_d$) CAN BE FOUND THROUGH FOLLOWING FORMULA BY INPUTTING INITIAL TEMPERATURE ($T_0$) AND INITIAL HUMIDITY ($H_0$). $t_d = \alpha \times a(T_1)/a(T_0) \times \beta \times H_1/(H-H_0) \times t_1 + t_2$ |

| DECONTAMINATION TIME | $t_d$ |
|---|---|
| EFFECTIVE DECONTAMINATION TIME AT REFERENCE TEMPERATURE-HUMIDITY | $t_1$ |
| TIME FOR SUPPLEMENTING TEMPERATURE-HUMIDITY SENSOR ERROR | $t_2$ |
| INITIAL TEMPERATURE INSIDE DEVICE | $T_0$ |
| INITIAL HUMIDITY INSIDE DEVICE | $H_0$ |
| REFERENCE TEMPERATURE | $T_1$ |
| REFERENCE HUMIDITY | $H_1$ |
| SET DECONTAMINATION HUMIDITY | $H$ |
| SATURATED WATER VAPOR AMOUNT AT INITIAL TEMPERATURE | $a(T_0)$ |
| SATURATED WATER VAPOR AMOUNT AT INITIAL HUMIDITY | $a(T_1)$ |
| TEMPERATURE COEFFICIENT | $\alpha$ |
| HUMIDITY COEFFICIENT | $\beta$ |

(56) References Cited

U.S. PATENT DOCUMENTS

| | | | | |
|---|---|---|---|---|
| 2011/0058986 A1* | 3/2011 | Yokoi | ............... | A61L 2/0094 422/111 |
| 2011/0091354 A1 | 4/2011 | Schwartz et al. | | |
| 2011/0281514 A1* | 11/2011 | Haugen | ............ | B08B 15/023 454/57 |
| 2015/0191766 A1* | 7/2015 | Kobayashi | ............ | A61L 2/22 435/309.1 |

FOREIGN PATENT DOCUMENTS

| | | |
|---|---|---|
| FR | 2 889 960 | 3/2007 |
| GB | 2 223 678 | 4/1990 |
| JP | 2009-502370 | 1/2009 |
| JP | 2011-167405 | 9/2011 |
| JP | 2012-61045 | 3/2012 |
| WO | 2012/033850 | 3/2012 |

OTHER PUBLICATIONS

English machine translation of JP 201167405 provided by EPO entitled: "Description JP201167405," Sasae et al., 2011.*

"A Discussion of Biological Safety Cabinet Decontamination Methods: Formaldehyde, Chlorine Dioxide, and Vapor Phase Hydrogen Peroxide," ABSAorg., Applied Biosafety vol. 16, No. 1, 2011.

Material Safety Data Sheet "HemaPeroxy Liquid Disinfectant,".

"How to decontaminate a biological safety cabinet (BSC),".

International Search Report issued in E.P.O. Patent Application No. 15177034.4, dated Dec. 23, 2015.

Office Action issued in Japan Counterpart Patent Appl. No. 2014-147883, dated Nov. 22, 2016 , along with an English translation thereof.

Office Action issued in European Patent Office (EPO) Counterpart Patent Appl. No. 15177034.4, dated May 14, 2019.

* cited by examiner

FIG. 1

|     | PREFERENCE |
| --- | --- |
| (a) | REFERENCE TEMPERATURE ($T_1$) AND REFERENCE HUMIDITY ($H_1$) SET, EFFECTIVE DECONTAMINATION TIME ($t_1$) AT SET DECONTAMINATION HUMIDITY (H) MEASURED MULTIPLE TIMES AND ESTABLISHED. |
| (b) | DRUG SPRAY AMOUNT FOUND FROM RATIO OF REFERENCE HUMIDITY ($H_1$) AND POSSIBLE HUMIDITY TO REFERENCE TEMPERATURE ($T_1$) AND SATURATED WATER VAPOR AMOUNT $a(T_1)$. |
| (c) | DRUG SPRAY AMOUNT FOUND FROM RATIO OF INITIAL HUMIDITY ($H_0$) AND POSSIBLE HUMIDITY TO INITIAL TEMPERATURE ($T_0$) AND SATURATED WATER VAPOR AMOUNT $a(T_0)$. |
| (d) | DRUG RATIO OF REFERENCE TEMPERATURE-HUMIDITY AND INITIAL TEMPERATURE-HUMIDITY FOUND FROM RATIOS OF (b) AND (c). |
| (e) | INITIAL TEMPERATURE-HUMIDITY AT (c) HUMIDIFIED WITH DRUG UP TO SET DECONTAMINATION HUMIDITY (H), EFFECTIVE DECONTAMINATION TIME MEASURED MULTIPLE TIMES AND ESTABLISHED. |
| (f) | RATIO OF DRUG IN (d) MULTIPLIED BY EFFECTIVE DECONTAMINATION TIME ($t_1$) IN (a). |
| (g) | WEIGHTING TEMPERATURE AND HUMIDITY, TEMPERATURE COEFFICIENT ($\alpha$) AND HUMIDITY COEFFICIENT ($\beta$) FOUND AND MULTIPLIED SO THAT (f) $\neq$ (e). |
| (h) | ADD TIME ($t_2$) FOR SUPPLEMENTATION EQUIVALENT TO ERROR OF HUMIDITY GAUGE SENSOR IN (g). |
| (i) | ANY DECONTAMINATION TIME ($t_d$) CAN BE FOUND THROUGH FOLLOWING FORMULA BY INPUTTING INITIAL TEMPERATURE ($T_0$) AND INITIAL HUMIDITY ($H_0$).<br>$t_d = \alpha \times a(T_1)/a(T_0) \times \beta \times H_1/(H-H_0) \times t_1 + t_2$ |

| | |
|---|---|
| DECONTAMINATION TIME | $t_d$ |
| EFFECTIVE DECONTAMINATION TIME AT REFERENCE TEMPERATURE-HUMIDITY | $t_1$ |
| TIME FOR SUPPLEMENTING TEMPERATURE-HUMIDITY SENSOR ERROR | $t_2$ |
| INITIAL TEMPERATURE INSIDE DEVICE | $T_0$ |
| INITIAL HUMIDITY INSIDE DEVICE | $H_0$ |
| REFERENCE TEMPERATURE | $T_1$ |
| REFERENCE HUMIDITY | $H_1$ |
| SET DECONTAMINATION HUMIDITY | H |
| SATURATED WATER VAPOR AMOUNT AT INITIAL TEMPERATURE | $a(T_0)$ |
| SATURATED WATER VAPOR AMOUNT AT INITIAL HUMIDITY | $a(T_1)$ |
| TEMPERATURE COEFFICIENT | $\alpha$ |
| HUMIDITY COEFFICIENT | $\beta$ |

ULTRASONIC DECONTAMINATION DEVICE

TECHNICAL FIELD

The present invention relates to a device and method for decontaminating the interior of a biosafety cabinet using a drug considered to be safe for humans.

BACKGROUND ART

When a human-infecting virus or bacterium is treated, the World Health Organization (WHO) guidelines for laboratory biosafety are a basis for stipulating that the treatment be done in a contained environment classified and defined according to danger as biosafety (BS) level 1, BS level 2, BS level 3, or BS level 4. Furthermore, cases in which BS level 2 involves an aerosol or cases of BS level 3 or BS level 4 must be handled in a biosafety cabinet (also referred to as a "BSC" below) suitable for the level.

For cases dealing with genetically modified organisms, it is also stipulated that the organisms be treated in a BSC for containment, as the Cartagena Protocol on Biosafety (an agreement on biological diversity) has come into effect.

Furthermore, a BSC requires periodic maintenance in order to continually use the BSC safely. Before maintenance is performed, the interior of the BSC must be decontaminated for the purpose of preventing worker infection and preventing exposure to harmful microorganisms.

In addition to the above, JIS K 3800:2009 stipulates that a BSC interior be decontaminated in the following cases.
   a) Before a periodic inspection or safety check
   b) Before a HEPA filter replacement
   c) Before the cabinet is moved
   d) When the interior has been heavily contaminated
   e) When the intended purpose has changed
   f) In other necessary cases The range of BSC decontamination includes the inside of a work area, a circulated air HEPA filter, an exhaust HEPA filter, and the inside of a duct leading to these HEPA filters (also referred to as "the interior of the BSC" below).

For many years since 1939 when BSCs came into use, formalin fumigation has been used to decontaminate the interiors of BSCs (Non-Patent Document 1).

Formalin fumigation is performed by a procedure of heating and fuming a small amount of paraformaldehyde and water in the condition of rigorous curing. A BSC fan is sometimes operated to fill the BSC interior with formalin. After leaving the BSC for approximately one day in this state, neutralization and exhausting are performed.

Furthermore, when paraformaldehyde crystals thereafter adhere to surfaces inside the BSC as white powder, the surfaces must be repeatedly wiped with water many times because the crystals are toxic and corrosive. This decontamination work requires approximately two days.

Formalin fumigation of BSC interiors has been used for at least 70 years up to the present day. However, in formalin fumigation, vapor containing formaldehyde is created, and this vapor is harmful to the human body and is designated as a deleterious substance not for medicinal use under the Poisonous and Deleterious Substances Control Law of Japan. Formaldehyde is also specified as a specific class I designated chemical substance (a carcinogen) under the 2012 Chemical Substances Management Act of Japan. In recent years, this substance has been specified by the World Health Organization as a substance that causes leukemia and lymphoma. Verifications that this substance is harmful to humans have been made internationally, stipulations in multiple countries have increased, and there is demand for a decontamination method to replace formalin fumigation.

A method of using chlorine dioxide gas and hydrogen peroxide vapor has been developed as an alternative decontamination method.

However, chlorine dioxide gas is highly toxic with a control standard value of 0.1 ppm, a more severe value than a control standard value of formalin, 0.75 ppm. Similar to formalin, chlorine dioxide gas requires rigorous curing and must be neutralized by sodium thiosulfate and exhausted. The device is also expensive at typically 500,000 to 10,000,000 yen.

With a method using hydrogen peroxide vapor, an approximately 35% hydrogen peroxide solution is boiled to create vapor. Hydrogen peroxide vapor, which is highly toxic, requires rigorous curing and has a control standard value of 1.0 ppm. Hydrogen peroxide, said to not be carcinogenic to humans, is not listed in the carcinogens of the IARC, the NTP, or the OSHA, but is classified as A3 (no cases of causing cancer in humans have been confirmed, but carcinogenic effects in lab animals have been established) in the categories of the ACGIH (Non-Patent Document 2). The device is also expensive at typically 4,000,000 to 10,000,000 yen.

Thus, the alternative method of formalin fumigation has many problems in terms of safety and cost, and formalin fumigation remains mainstream.

PRIOR ART DOCUMENTS

Non-Patent Documents

[Non-Patent Document 1]
"A Discussion of Biological Safety Cabinet Decontamination Methods: Formaldehyde, Chlorine Dioxide, and Vapor Phase Hydrogen Peroxide," ABSAorg. Vol. 16, No. 1, 2011
[Non-Patent Document 2]
THE AMERICAN CONFERENCE OF GOVERNMENTAL INDUSTRIAL HYGIENISTS

SUMMARY OF THE INVENTION

Problems to be Solved by the Invention

The purpose of the present invention is to provide a device and method for decontaminating the interior of a biosafety cabinet using a drug considered to be safe for humans.

Means for Solving these Problems

In view of the problems with the prior art described above, the inventors have discovered as a result of earnest research that droplets (a dry fog) of extremely small diameter can be created when a peracetic acid disinfectant is atomized by ultrasound, and the interior of a biosafety cabinet can be efficiently decontaminated by further gasifying these droplets, circulating the gasified peracetic acid through the BSC interior, and exhausting some of the gasified peracetic acid out to the exterior.

Specifically, the present invention provides the following.
[1] A device for decontaminating the interior of a biosafety cabinet, the decontamination device comprising:
   an ultrasonic atomizer for atomizing a peracetic acid disinfectant by ultrasonic vibration and releasing droplets;
   a diffusion fan;
   a circulation fan;
   a temperature-humidity sensor; and
   a controller.

[2] The decontamination device according to [1], wherein the peracetic acid disinfectant is a mixture of peracetic acid, hydrogen peroxide, acetic acid, and water.

[3] The decontamination device according to [1] or [2], wherein the controller has an automatic decontamination time computing function.

[4] The decontamination device according to any of [1] through [3], wherein the controller has an automatic decontamination time computing function for calculating decontamination time from only the temperature and humidity inside the biosafety cabinet to be decontaminated.

[5] A method for decontaminating the interior of a biosafety cabinet, said method comprising the steps of:

installing an ultrasonic atomizer for atomizing a peracetic acid disinfectant by ultrasonic vibration and releasing droplets, a diffusion fan, a temperature-humidity sensor, and a circulation fan in a work area of the biosafety cabinet;

releasing droplets by activating said ultrasonic atomizer and atomizing the peracetic acid disinfectant by ultrasound, and gasifying said droplets; and circulating the gasified peracetic acid (peracetic acid gas) in the interior of said biosafety cabinet.

[6] The method according to [5], wherein the peracetic acid gas is circulated in the interior of the biosafety cabinet by the circulation fan.

[7] The method according to [5] or [6], wherein some of the peracetic acid gas circulated in the interior of the biosafety cabinet is exhausted to the exterior.

[8] The method according to [6] or [7], wherein the peracetic acid gas is circulated in the interior of the biosafety cabinet and partially exhausted to the exterior by operating the circulation fan and creating circulation of air leading from a work area into a duct, to a circulation HEPA filter, and back to the work area, and exhausting some of the air through an exhaust HEPA filter to the exterior.

[9] The method according to any of [5] through [8], wherein gasification of the droplets of the peracetic acid disinfectant is promoted by the diffusion fan.

[10] The method according to any of [5] through [9], wherein the humidity in the work area is controlled at 85 to 90%.

Effects of the Invention

In the decontamination device and decontamination method of the present invention, the inside of a work area, a circulated air HEPA filter, an exhaust HEPA filter, and the inside of a duct leading to these HEPA filters can be efficiently decontaminated by atomizing and gasifying a peracetic acid disinfectant by ultrasound, circulating the gasified peracetic acid to the interior of a biosafety cabinet, and exhausting some of the gasified peracetic acid to the exterior.

In the decontamination device and decontamination method of the present invention, it is possible to decontaminate the interior of a BSC while suppressing corrosion even if a corrosion-prone metal is used, because an oxide film is formed on the surface of the corrosion-prone metal by using gasified peracetic acid.

BRIEF DESCRIPTION OF THE DRAWINGS

FIG. 1 is an example of an algorithm that can be used in the decontamination device and decontamination method of the present invention;

MODE FOR CARRYING OUT THE INVENTION

In the present specification, the term "biosafety cabinet" (BSC) refers to a device having a structure in which a HEPA filter is attached to a draft chamber, the device being used for containing and safely treating harmful microorganisms. The term "biosafety cabinet" includes safety cabinets and biohazard countermeasure cabinets as well.

Biosafety cabinets are classified as three types: class I, class II, and class III, depending on the risk of the treated microorganisms. The biosafety cabinet that is the object of decontamination in the present invention is the class II type.

In the present specification, the term "the interior of the biosafety cabinet" means the inside of a work area, a circulation HEPA filter, an exhaust HEPA filter, and the inside of a duct leading to these HEPA filters.

One embodiment of the present invention is a device for decontaminating the interior of the biosafety cabinet, the decontamination device comprising an ultrasonic atomizer for atomizing a peracetic acid disinfectant by ultrasonic vibration and releasing droplets, a diffusion fan, a circulation fan, a temperature-humidity sensor, and a controller.

In the ultrasonic atomizer used in the present invention, an atomizing vibrator is vibrated and a liquid can be atomized by the ultrasound.

The atomizing vibrator used herein preferably has a piezoelectric element composed of piezoelectric ceramics, and an insulating resin film covering an adherend surface of the piezoelectric element, the adherend surface including a liquid-facing surface that faces a liquid. The atomizing vibrator is preferably disposed in a manner such that the liquid-facing surface faces the liquid and the insulating resin film is in contact with the liquid. The insulating resin film is preferably composed of a paraxylene polymer 5 to 20 μm in thickness, in which monomers are layered on the adherend surface of the piezoelectric element and polymerized together.

In the ultrasonic atomizer used in the present invention, the piezoelectric element is preferably plate-shaped, having: a piezoelectric ceramic plate having a first main surface, a second main surface, and side surfaces joining the main surfaces together; a first electrode layer spread on the first main surface, the first electrode layer extending to the second main surface via the side surfaces; and a second electrode layer which in the second main surface is separated from the first electrode layer, spread on the second main surface, and made to face the first electrode layer on the first main surface via the piezoelectric ceramic plate. The insulating resin film, which covers the adherend surface formed by the first main surface, the side surfaces, and the first electrode layer formed thereon, preferably has a configuration in which the piezoelectric element is disposed with the first main surface facing the liquid.

The piezoelectric ceramic plate is preferably an atomizing vibrator formed into dimensions so as to resonate in the thickness direction when an electric signal having a frequency of 1 to 5 MHz is applied between the first electrode layer and the second electrode layer.

This type of ultrasonic atomizer is disclosed in detail in Japanese Laid-open Patent Application No. 2011-36771, and the contents disclosed in this document can be incorporated by reference in the range of the present invention.

The ultrasonic atomizer in the present invention is connected to the controller and is activated and stopped by the control of the controller.

The ultrasonic atomizer in the present invention is preferably designed so that when the drug amount is insufficient, a low water level display is used to halt atomization while simultaneously stopping the countdown if the decontamination time is currently underway. Even safer is a design in which a pause setup is used and atomization is not immediately performed when the drug is replenished. After atomization, a decontamination time countdown is performed after the set humidity has again been reached.

The ultrasonic atomizer in the present invention preferably has a function for logging temperature and humidity, and takes recordings automatically every, e.g., one minute. The log records can be retained in CSV format of one file for each decontamination.

The peracetic acid disinfectant used in the present invention is preferably composed of a mixture of peracetic acid, hydrogen peroxide, acetic acid, and water.

In the peracetic acid disinfectant in the present invention, preferably, the peracetic acid content is 0.01 to 1.2 wt %, the hydrogen peroxide content is 0.06 to 4.8 wt %, the acetic acid content is 0.02 to 6.0 wt %, and the remnant is water.

Examples of the peracetic acid disinfectant that can be used in the present invention include, e.g., Actril (registered trademark in Japan) and Minncare (registered trademark in Japan) commercially available from MARCOR, other peracetic acid disinfectants, and the like.

In the present invention, droplets of extremely small diameter (micron size) can be created by causing the atomizing vibrator to vibrate in the previously-described ultrasonic atomizer and atomizing the peracetic acid disinfectant by means of the ultrasound. The center diameter of the droplets is preferably 3 to 15 μm and more preferably 3 to 10 μm. Such extremely small droplets, also referred to as a dry fog, have the characteristics of a fog that is not wet, and the device to be coated can therefore be coated effectively without being damaged by corrosion. Because the droplets do not wet the inside of the device, secondary contamination caused by wiping off the liquid can be prevented.

Because peracetic acid has a wide antibacterial spectrum, sporular bacteria, which could not be sterilized in a short time by the prior art method relying on hydrogen peroxide vapor, can be killed in a short time by using the device of the present invention.

The decontamination device of the present invention includes a diffusion fan. The diffusion fan has a fan motor, and the fan is rotated by the motive power of the motor. The diffusion fan can be connected to the ultrasonic atomizer. The diffusion fan equalizes the distribution of disinfectant particles in the BSC interior. In the decontamination device of the present invention, gasification of the peracetic acid disinfectant can be promoted by diffusing the droplets (dry fog) of the peracetic acid disinfectant using the diffusion fan. To efficiently gasify the droplets of peracetic acid disinfectant, the diffusion fan is preferably installed in the periphery of the nozzle of the ultrasonic atomizer. The distance at which the diffusion fan is installed from the nozzle is appropriately defined by the output of the diffusion fan, but the fan is preferably installed within, e.g., 10 cm from the nozzle.

In the decontamination device of the present invention, gasifying the droplets of the peracetic acid disinfectant makes it possible to also efficiently decontaminate the inside of the HEPA filter with peracetic acid gas, and to create free radicals to synergistically increase the decontamination effect.

The decontamination device of the present invention includes a circulation fan. The circulation fan has a fan motor, and the fan is rotated by the motive power of the motor. The circulation fan can circulate the peracetic acid gas created in the work area within the interior of the biosafety cabinet, and can exhaust some of the gas to the exterior. Specifically, the circulation fan is operated to circulate air from the work area into the duct, to the circulation HEPA filter, and back to the work area, and to create air of which some is exhausted to the exterior through the exhaust HEPA filter, whereby the peracetic acid gas can be circulated in the interior of the biosafety cabinet and some of the gas can be exhausted to the exterior.

The decontamination device of the present invention can include a catalyst fan. The catalyst fan is used after decontamination when decomposition of the hydrogen peroxide in the BSC must be accomplished in a short time. The catalyst fan has a fan motor and a catalyst, the fan is rotated by the motive power of the motor, and the fan efficiently passes outside air through the catalyst and decomposes the hydrogen peroxide.

The decontamination device of the present invention includes a temperature-humidity sensor. The temperature-humidity sensor, which is connected to the controller, transmits detected values of the measured temperature and humidity to the controller. The transmitted detected values are displayed on the controller in real time, and a record can be automatically acquired each minute. The acquired records (logs) can be recorded in USB memory of the controller as CSV files, and the data can be moved to an external computer and confirmed. The reliability of the temperature-humidity sensor can be preserved by calibration and support. In the present invention, the temperature-humidity sensor can be disposed in the interior of the BSC during decontamination, in the usual case, it can be disposed in an appropriate location inside the work area.

The decontamination device of the present invention includes a controller. The controller in the present invention is electrically connected with the ultrasonic atomizer, the diffusion fan, the temperature-humidity sensor, and in some cases the catalyst fan. The controller starts the running of the ultrasonic atomizer, starts the air-blowing by the diffusion fan, and uses the air-blowing by the independently operating circulation fan to perform the decontamination process. During the decontamination process, the controller activates or stops the ultrasonic atomizer on the basis of the values detected by the temperature-humidity sensor so that the humidity inside the work area detected by the temperature-humidity sensor is maintained at the humidity set in advance. When decontamination ends, the catalyst fan is activated to decompose the hydrogen peroxide in the BSC as necessary.

The controller of the present invention can include an automatic decontamination time computing function. Specifically, before the decontamination process is started, the temperature of the interior of the device to be decontaminated is measured by the temperature-humidity sensor, and the amount of saturated vapor at this temperature is calculated. Next, the humidity inside the device to be decontaminated is measured. The amount of water vapor inside the device to be decontaminated is calculated from the measured value of humidity and the amount of saturated vapor found as previously described. It is thereby possible to calculate how many peracetic acid disinfectant droplets can be sprayed inside the device to be decontaminated. Furthermore, the decontamination time can be derived from the amount of sprayed peracetic acid disinfectant thus calculated, using an algorithm. Here, the decontamination time is started from when the predetermined humidity that is set in advance and that should be preserved inside the work area is achieved, and is finished when the end of decontamination. Also, the algorithm is completed by comparing the results of many decontamination condition tests. FIG. 1 shows an example of an algorithm that can be used in the automatic decontamination time computing function that the controller of the present invention can have.

Due to the decontamination device of the present invention having this type of automatic decontamination time computing function, there is no need to excessively spray disinfectant, and the decontamination time can be derived from only the temperature and humidity of the interior of the equipment to be decontaminated, and a safe decontamination level can therefore be provided with no decontamination mistakes regardless of who is using the device.

The following modes can be used in the controller in the present invention: a manual mode in which a set humidity, a humidity maintenance time, and a catalyst fan activation time can be inputted manually and the decontamination process can be performed; a memory mode in which up to three types of preset numerical values can be recorded; an auto mode that can be used merely by installing the temperature-humidity sensor, without implementing any settings; and a continuous mode in which decontamination is continued until the set decontaminant is all used up.

The decontamination device of the present invention can be configured such that the ultrasonic atomizer, the temperature-humidity sensor, the diffusion fan, and in some cases the catalyst fan are all electrically connected to the controller.

The decontamination device of the present invention can be configured comprising the controller and a device in which at least one of the temperature-humidity sensor, the diffusion fan, and the catalyst fan is provided to the ultrasonic atomizer and the devices are integrated together. In this case, the integrated device and the controller can be electrically connected. Otherwise, the integrated device can be controlled by the controller through wireless communication.

Another embodiment of the present invention is a method for decontaminating the interior of a biosafety cabinet, the method comprising the steps of:

installing an ultrasonic atomizer for atomizing a peracetic acid disinfectant and releasing droplets by ultrasonic vibration, a diffusion fan, a temperature-humidity sensor, and a circulation fan in a work area of a biosafety cabinet;

releasing droplets by activating the ultrasonic atomizer and atomizing the peracetic acid disinfectant by ultrasound, and gasifying the droplets; and circulating the gasified peracetic acid (peracetic acid gas) in the interior of the biosafety cabinet and exhausting some of the gasified peracetic acid to the exterior.

The method of the present invention is intended to decontaminate a BSC interior using a peracetic acid disinfectant considered to be safe for humans, and because the peracetic acid disinfectant is gasified it is not an irritant.

FIG. 1 shows a non-limiting example of the decontamination device of the present invention and a decontamination method using this device.

In the decontamination method of the present invention, an ultrasonic atomizer, a diffusion fan, a temperature-humidity sensor, and a circulation fan are installed in a work area of a BSC. At this time, curing tape or the like is preferably used to weather-strip a ventilation port for BSC circulation near the working surface.

The ventilation port which has been the weather-stripped for BSC circulation is opened in preferably two places, and circulation fans are secured facing downward in positions approximately 5 to 10 cm from both sides of the two places. It is preferable to close the glass surface in front of the work area and weather-strip the gaps in the top, bottom, left, and right using curing tape or the like.

In this state, when the circulation fans (preferably two of them) are activated, circulated air is produced, traveling from the work area, to the duct, the circulation HEPA filter, and back to the work area. Thus, air is circulated by the circulation fans, whereby the gasified peracetic acid disinfectant can be circulated through the BSC interior, i.e., from the work area into the duct, and through the circulation HEPA filter back to the work area, and some of the disinfectant can be exhausted to the exterior through the exhaust HEPA filter.

The exterior of the exhaust HEPA filter is cured, or the damper is closed. At this time it is preferable to not completely hermetically seal the environment and to let air leak out a little bit at a time. In the case of weather-stripping, it is preferable for gaps of approximately 1 to 2 $cm^2$ to be left. By letting air leak out in this manner, some of the gasified peracetic acid disinfectant can be exhausted to the exterior of the BSC (other than a damper or curing in FIG. 1) through the exhaust HEPA filter. When the peracetic acid gas is not fully exhausted from the BSC, the peracetic acid disinfectant cannot be newly atomized because the inside of the work area reaches a humidity of approximately 80% in a short time. Even if the disinfectant is atomized, it decomposes into acetic acid and oxygen. Exhausting some of the peracetic acid gas out of the BSC makes it possible to continuously atomize the peracetic acid disinfectant and to increase the decontaminating effect.

When the peracetic acid gas is exhausted from the BSC, gas leaks into the room, but the room remains an environment in which humans can work because the peracetic acid gas is not an irritant.

Preferably, the amount of peracetic acid disinfectant used in the ultrasonic atomizer is normally 500 mL (effective used amount: 450 mL) when the BSC has an opening of 1.3 m, and normally 650 mL (effective used amount: 600 mL) when the BSC has an opening of 1.8 m.

Next, the ultrasonic atomizer, the diffusion fan, the temperature-humidity sensor, and the controller are operated.

The particle diameter of mist sprayed by the ultrasound is controlled to 10 μm or less, and preferably to 5 μm or less. Droplets of a particle diameter of 10 μm or less constitute a mist referred to as a dry fog in which the droplets when touched rebound while stably retaining shape, or in other words, the droplets do not wet anything.

In the method of the present invention, the diffusion fan is preferably used to promote gasification of the droplets (dry fog) of the peracetic acid disinfectant. To efficiently gasify the droplets of the peracetic acid disinfectant, the diffusion fan is preferably installed in the periphery of the nozzle of the ultrasonic atomizer. The distance at which the diffusion fan is installed from the nozzle is appropriately defined by the output of the diffusion fan, but the fan is preferably installed within, e.g., 10 cm from the nozzle.

Due to the gasification of the droplets of the peracetic acid disinfectant in the decontamination method of the present invention, the insides of the HEPA filters can also be efficiently decontaminated by peracetic acid gas passing through, and free radicals can be created to synergistically increase the decontaminating effect.

The peracetic acid disinfectant is highly corrosive and therefore could not be used in a corrosion-prone metal (iron, copper, etc.), but in the method of the present invention, an oxide film (an oxide film for iron and a verdigris film for copper) is formed on the surface of the corrosion-prone metal by gasifying the peracetic acid disinfectant, and the oxide film has the effect of preventing corrosion. Therefore, with the method of the present invention, even if a corrosion-prone metal is used in the components and the like in the BSC interior, the BSC interior can be decontaminated while corrosion is suppressed (outlets, sensor surfaces, and the like are preferably cured in advance).

Having been quickly gasified by the diffusion fan, the peracetic acid disinfectant is carried by the airflow of the circulation fan to circulate from the work area to the duct, the circulation HEPA filter, and back to the work area. Due to the inside of the work area having slight negative pressure and a small amount of outside air entering, and due to the gasification, the increased vapor components are exhausted out through the exhaust HEPA filter.

Thus, in the method of the present invention, peracetic acid gas passes through the insides of the work area, the duct, the circulation HEPA filter, and the exhaust HEPA filter (i.e., the BSC interior), and these passages can be decontaminated.

In such a state, decontamination of the BSC interior is continued until 500 mL (approximately 450 mL excluding dead volume) is gasified.

When the droplets of the peracetic acid disinfectant continue to be gasified and the humidity inside the BSC approaches 100%, the droplets turn to mist and further form dew. When the gas of the peracetic acid disinfectant forms dew, the gas condenses to be needlessly consumed, and the disinfectant in mist form gets trapped in the HEPA filters and does not spread throughout the entire BSC interior. Therefore, in the method of the present invention, the humidity in the BSC interior, and typically inside the work area, is preferably controlled to 85 to 90%.

A large temperature difference is also a cause of dew formation. The controlled humidity is preferably set with some extent of temperature difference and decontaminating effect taken into account.

Decontaminated BSCs will often be used for many years, and HEPA filter interiors have different amounts of moisture depending on the rate of clogging of the HEPA filters and the environments in which the HEPA filters are placed. For these reasons, different times are required to gasify 500 mL (effective used amount: 450 mL) of the peracetic acid disinfectant, but the time is commonly approximately 24 hours±4 hours.

For the humidity sensor, normal sensors are not expected to be used in peracetic acid gas and are therefore not durable, the values drift, and the sensor breaks. In view of this, it is preferable to use a humidity sensor and circuitry that exhibit durability in peracetic acid gas, by confirming an appropriate method of treating the surface of the sensor element and designing the circuitry with the characteristics of the peracetic acid gas taken into account.

In the decontamination method of the present invention, the controller can include the previously-described automatic decontamination time computing function. Refer to the explanation of the decontamination device of the present invention and FIG. 1 for details.

The decontaminating effect is confirmed by installing a biological indicator (referred to as a "BI" below) in the work area, in the duct, and on the outer side of the exhaust HEPA filter (the damper or the inner side of the curing). Specifically, sporular bacteria, said to be difficult to kill, are entangled in filter paper within glassine paper or the like and put living into a BI, and after decontamination, the bacteria are cultivated in a designated culture medium and decontamination is confirmed by the change in color of the culture medium. Though the bacterias which are put in the BIs placed inside the work area and inside the duct in the BSC interior are killed readily, it is appropriate that the killing done by the BI on the exterior of the exhaust HEPA filter, which has the worst conditions, be used as an indicator of the decontaminating effect in order to confirm that the HEPA filters have been decontaminated.

In the method of the present invention, there is no particular need for neutralization or exhaust after decontamination has ended. For safety reasons, one cannot enter the room during decontamination due to formalin fumigation, chlorine dioxide gas, and hydrogen peroxide vapor, but the method of the present invention has a great advantage in that other work can be performed without issue despite some odor of acetic acid.

EXAMPLES

The present invention is further described below using examples, but the scope of the present invention is not limited to these examples.

Example 1

Using the decontamination device of the present invention (a decontamination device comprising an ultrasonic atomizer for gasifying a peracetic acid disinfectant by ultrasonic vibration and releasing droplets, a diffusion fan, a circulation fan, a temperature-humidity sensor, and a controller), 450 mL of a peracetic acid disinfectant (Actril) was gasified and a BSC was decontaminated.

The BSC used was a biohazard cabinet MHE-123AJ (SANYO).

BI $10^6$ (ETIGAM ES sporestrips (Lot#: GST-436)) was used for the indicator bacteria (BI), and a TSB culture medium (SporVIEW Culture Media (Lot#: 12397)) was used for the culture medium.

BIs were installed in the four corners and center outside of the exhaust HEPA filter (the inner sides of the exhaust port weather-stripped while a 2 $cm^2$ leak port was provided), for a total of five places.

The initial temperature and humidity before the decontamination test was as follows.
Initial Temperature
  Inside work area: 24.9° C.
  Outside exhaust HEPA filter: 24.5° C.
Initial Humidity
  Inside work area: 62%
  Outside exhaust HEPA filter: 66%

Figure 2:
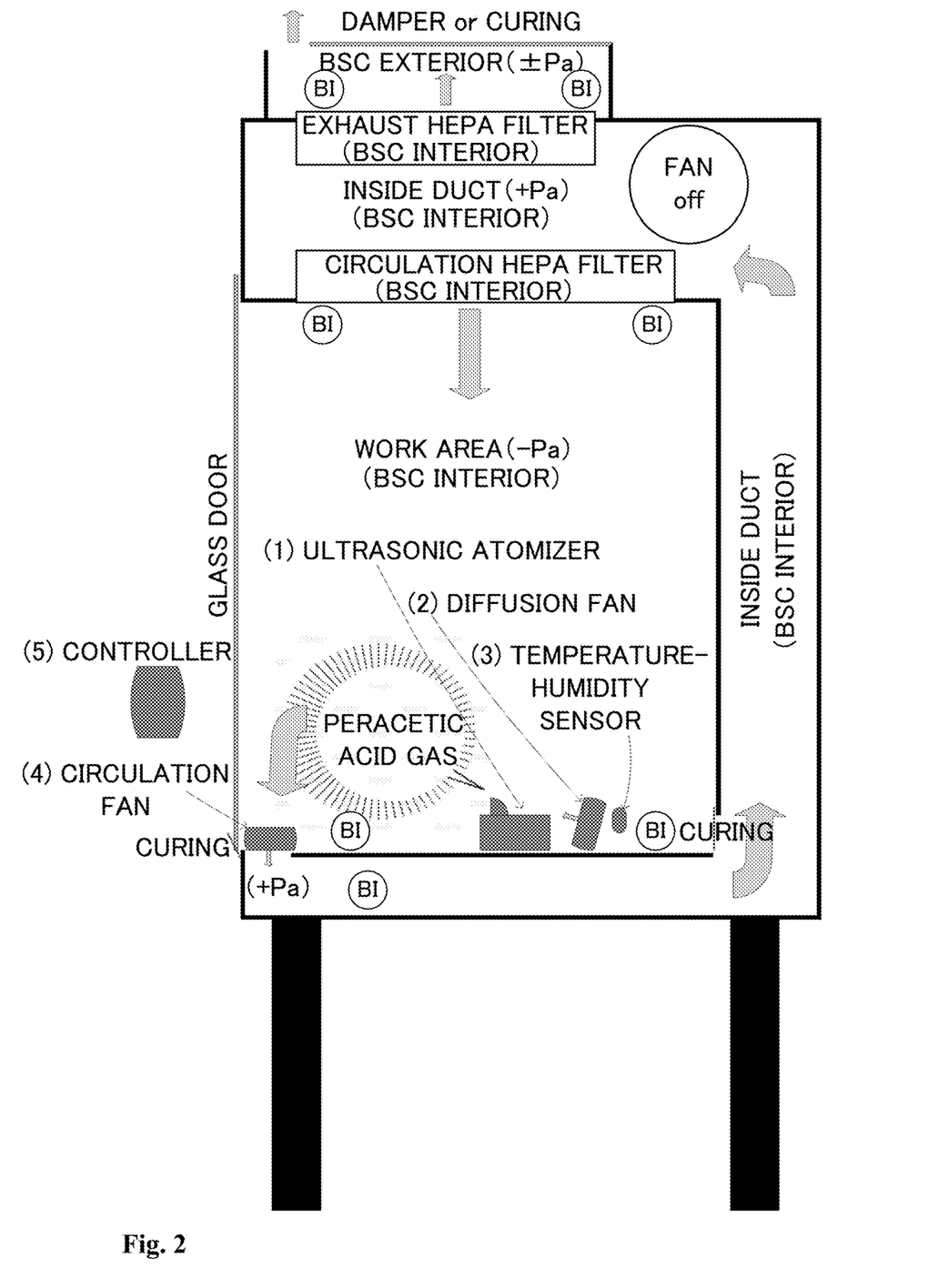
FIG. 2 is a non-limiting example of the decontamination device of the present invention and the decontamination method using this device.
Figure 3:
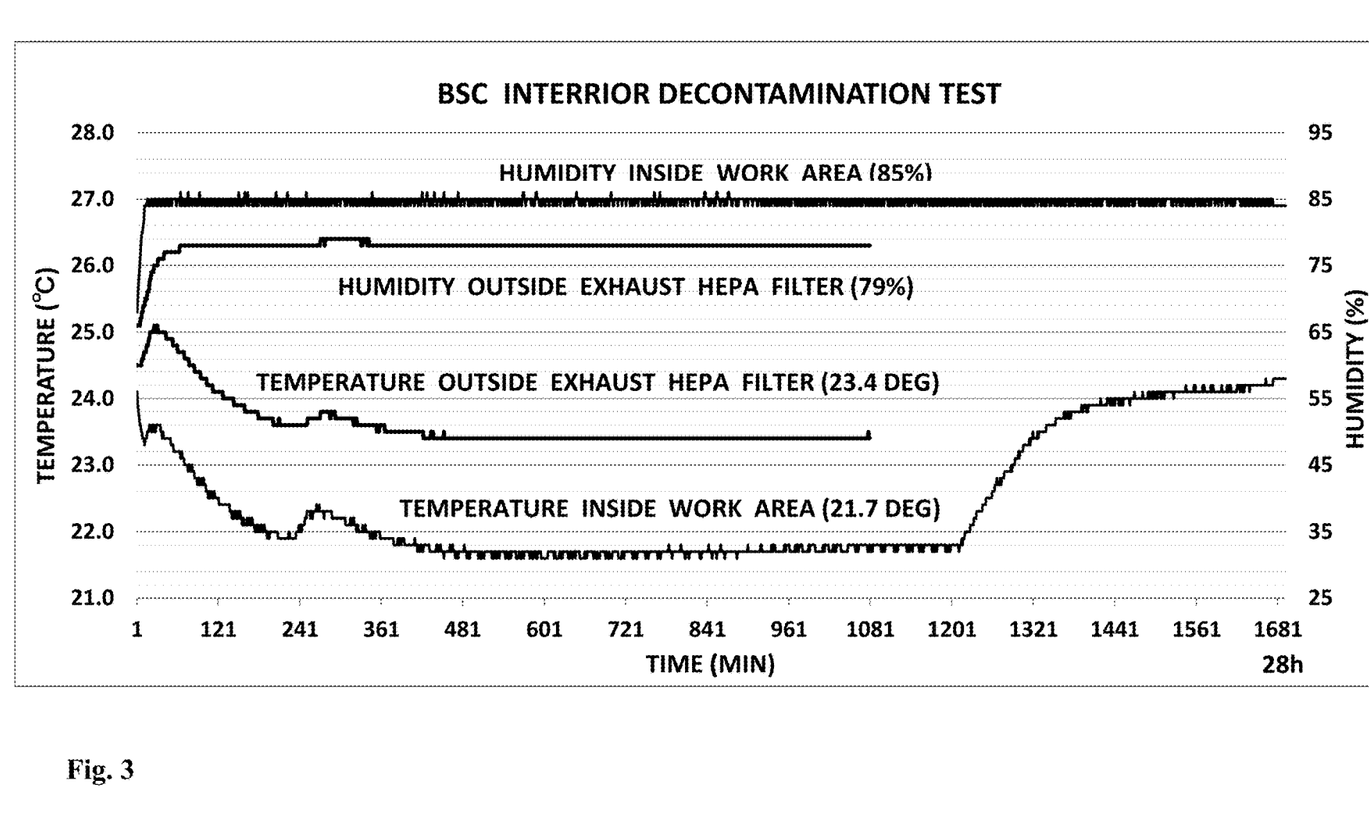
FIG. 3 shows the changes in temperature and humidity both inside a work area and outside an exhaust HEPA filter in a decontamination test of Example 1.

The set humidity inside the work area was 85%, and decontamination was performed for 28 hours until 450 mL of the peracetic acid disinfectant had gasified. FIG. 3 shows the changes in the temperature and humidity both inside the work area and outside the exhaust HEPA filter during decontamination testing.

After decontamination, the BIs were cultured for seven days by a designated culture medium, and a decisive determination was made. The results are as shown in Table 1 below.

TABLE 1

| BI Installed Location | Position | Culturing Effect |
|---|---|---|
| Outside exhaust HEPA filter | top right | negative |
| | top left | negative |
| | center | negative |
| | bottom right | negative |
| | bottom left | negative |

As shown in Table 1, it is demonstrated that the interior of a BSC can be effectively decontaminated by the device and decontamination method of the present invention.

The invention claimed is:

1. A method for decontaminating the interior of a biosafety cabinet, the method comprising:
    providing an exhaust HEPA filter in the interior of the biosafety cabinet;
    providing an interior duct within the interior of the biosafety cabinet;
    installing an ultrasonic atomizer, having a nozzle, for atomizing a peracetic acid disinfectant by ultrasonic vibration and releasing droplets, a diffusion fan, a temperature-humidity sensor, and a circulation fan in a work area of the biosafety cabinet, the diffusion fan being connected to the ultrasonic atomizer, wherein the diffusion fan is installed at a periphery of the nozzle of the ultrasonic atomizer;
    releasing droplets by activating the ultrasonic atomizer and atomizing the peracetic acid disinfectant by ultrasound, and gasifying the droplets; and
    circulating the gasified peracetic acid in the interior of the biosafety cabinet,
    providing the work area with a return inlet configured to return the circulated gasified peracetic acid into the work area and an outlet configured to convey the circulated gasified peracetic acid from the work area,
    wherein an impending flow of the peracetic acid gas at an exit of the interior duct is partially returned to the work area through the return inlet while at least a portion of the impending flow of the peracetic acid gas is exhausted to the outside via only the exhaust HEPA filter without being recirculated through the work area and at a position that is proximate the return inlet.

2. The method according to claim 1, wherein the peracetic acid gas is circulated in the interior of the bio safety cabinet by the circulation fan.

3. The method according to claim 2, wherein the peracetic acid gas is circulated in the interior of the biosafety cabinet and partially exhausted to the exterior by operating the circulation fan and creating circulation of air leading from the work area into the interior duct, to a circulation HEPA filter, and back to the work area, and exhausting some of the air through an exhaust HEPA filter to the exterior.

4. The method according to claim 1, wherein gasification of the droplets of the peracetic acid disinfectant is promoted by the diffusion fan.

5. The method according to claim 1, wherein the humidity in the work area is controlled at 85 to 90%.

6. The method according to claim 1, further comprising installing the diffusion fan within 10 cm of the nozzle.

* * * * *